(12) United States Patent
Nabata et al.

(10) Patent No.: US 7,785,654 B2
(45) Date of Patent: Aug. 31, 2010

(54) METHOD OF PRODUCING COSMETICS-IMPREGNATED SHEET

(75) Inventors: Yoshiyuki Nabata, Tochigi (JP);
Takeshi Nakajima, Togichi (JP);
Hidehiko Nakayama, Tochigi (JP);
Masayasu Sato, Tochigi (JP); Takashi Kawai, Tochigi (JP); Mitsuo Shimizu, Tokyo (JP)

(73) Assignee: Kao Corporation, Tokyo (JP)

( * ) Notice: Subject to any disclaimer, the term of this patent is extended or adjusted under 35 U.S.C. 154(b) by 1823 days.

(21) Appl. No.: 10/471,564

(22) PCT Filed: Mar. 14, 2002

(86) PCT No.: PCT/JP02/02426

§ 371 (c)(1),
(2), (4) Date: May 24, 2004

(87) PCT Pub. No.: WO02/074262

PCT Pub. Date: Sep. 26, 2002

(65) Prior Publication Data

US 2004/0191280 A1    Sep. 30, 2004

(30) Foreign Application Priority Data

Mar. 16, 2001   (JP)  .............................. 2001-076814

(51) Int. Cl.
*A45D 40/28*  (2006.01)
*A61Q 1/00*   (2006.01)
*A61F 13/02*  (2006.01)
*A61K 8/00*   (2006.01)
*A61K 8/18*   (2006.01)

(52) U.S. Cl. .................. 427/2.3; 427/2.1; 427/2.31; 424/59; 424/61; 424/64; 424/69; 132/30; 132/320

(58) Field of Classification Search ................ 427/2.31, 427/2.3, 2.1; 424/401, 402, 443–447, 59, 424/61, 64, 69; 132/300, 320; 514/937–943, 514/946

See application file for complete search history.

(56) References Cited

U.S. PATENT DOCUMENTS 3,619,842 A   *   11/1971   Maierson .................. 15/104.93

(Continued)

FOREIGN PATENT DOCUMENTS

JP            5-31429         2/1993

(Continued)

*Primary Examiner*—Timothy H Meeks
*Assistant Examiner*—Cachet I Sellman
(74) *Attorney, Agent, or Firm*—Oblon, Spivak, McClelland, Maier & Neustadt, L.L.P.

(57) ABSTRACT

A process for producing a cosmetic-impregnated sheet which comprises applying and infiltrating a cosmetic base to and into a base sheet having on the surface thereof a retentive sheet capable of absorbing and retaining the cosmetic base at a shear rate of $10^2$ to $10^6$ s$^{-1}$, the cosmetic base being applied to and infiltrated into the retentive sheet of the base sheet, and the cosmetic base, when subjected to a steady shear deformation at a shear rate of 2 s$^{-1}$ for 100 seconds followed by a steady shear deformation at a stepwise increased shear rate of 20 s$^{-1}$, showing no shear stress growth or showing such a shear stress growth that the difference between the peak shear stress B at a shear rate of 20 s$^{-1}$ and the equilibrium shear stress A at the same shear rate, B−A, is 20% or smaller of the equilibrium shear stress A in the transition between the two shear rates.

19 Claims, 1 Drawing Sheet

U.S. PATENT DOCUMENTS

| | | | | |
|---|---|---|---|---|
| 3,957,969 | A | * | 5/1976 | Fujiyama et al. ............... 424/64 |
| 4,108,185 | A | * | 8/1978 | Boulogne et al. .............. 401/88 |
| 4,424,204 | A | * | 1/1984 | Minamino et al. ............ 424/63 |
| 4,439,457 | A | * | 3/1984 | Kuy ........................... 426/310 |
| 4,743,441 | A | * | 5/1988 | Takema et al. ................. 424/47 |
| 6,129,978 | A | | 10/2000 | Caldwell |
| 6,766,817 | B2 | | 7/2004 | da Silva |

FOREIGN PATENT DOCUMENTS

| | | | | |
|---|---|---|---|---|
| JP | 7-189196 | | | 7/1995 |
| JP | 8-266997 | | | 10/1996 |
| JP | 10-8003 | | | 1/1998 |
| JP | 11-605 | | | 1/1999 |
| JP | 11-49641 | | | 2/1999 |
| JP | 11049641 | A | * | 2/1999 |
| JP | 11-286081 | | | 10/1999 |
| JP | 2000-44427 | | | 2/2000 |
| JP | 2000-70816 | | | 3/2000 |
| JP | 2000-218207 | | | 8/2000 |
| JP | 2000-256164 | | | 9/2000 |
| JP | 2000-354814 | | | 12/2000 |
| JP | 2001-2528 | | | 1/2001 |
| JP | 2001002528 | A | * | 1/2001 |
| JP | 2002255736 | A | * | 9/2002 |
| WO | 98/15262 | | | 4/1998 |

* cited by examiner

METHOD OF PRODUCING COSMETICS-IMPREGNATED SHEET

TECHNICAL FIELD

The present invention relates to a process for producing a cosmetic-impregnated sheet having a base sheet coated and impregnated with a thixotropic cosmetic base.

BACKGROUND ART

JP-A-11-286081 discloses a composite sheet comprising a polypropylene spun-bonded nonwoven fabric, a moisture-permeable and waterproof polyethylene film, and a viscose rayon nonwoven fabric superposed in this order, the spun-bonded nonwoven fabric being coated with an oil base, such as a composition for an oil-based foundation. JP-T-2000-503681 discloses a cosmetic applicator having a porous or absorbent sheet impregnated with an oil-in-water emulsion composition.

According to these publications, the oil base or emulsion composition is applied to and infiltrated into the base sheet with a coating means such as a gravure coater, a floating knife, or a doctor blade. However, where the base composition to be applied and infiltrated is such a viscous substance having thixotropic properties, the base composition may be applied only on the surface of the base sheet and have great difficulty in penetrating into the inside of the base sheet.

Accordingly, it is an object of the present invention to provide a process for producing a cosmetic-impregnated sheet whereby a thixotropic cosmetic is applied and infiltrated with ease.

DISCLOSURE OF THE INVENTION

The object of the present invention is accomplished by providing a process for producing a cosmetic-impregnated sheet which comprises applying and infiltrating a cosmetic base to and into a base sheet having on the surface thereof a retentive sheet capable of absorbing and retaining the cosmetic base at a shear rate of $10^2$ to $10^6$ s$^{-1}$, the cosmetic base being applied to and infiltrated into the retentive sheet of the base sheet, and the cosmetic base, when subjected to a steady shear deformation at a shear rate of 2 s$^{-1}$ for 100 seconds followed by a steady shear deformation at a stepwise increased shear rate of 20 s$^{-1}$, showing no shear stress growth or showing such a shear stress growth that the difference between the peak shear stress at a shear rate of 20 s$^{-1}$ and the equilibrium shear stress at the same shear rate is 20% or smaller of the equilibrium shear stress, in the transition between the two shear deformations.

BEST MODE FOR CARRYING OUT THE INVENTION

The present invention will be described based on its preferred embodiments. The cosmetic base which can be used in the present invention exhibits thixotropic properties and comprises, for example, an oily liquid, an emulsified liquid or an aqueous liquid. Examples of the cosmetic base are various kinds of skin care creams, UV protection creams, antiperspirants, foundations, lipstick bases, cleansers, and makeup removers.

Figure 1:
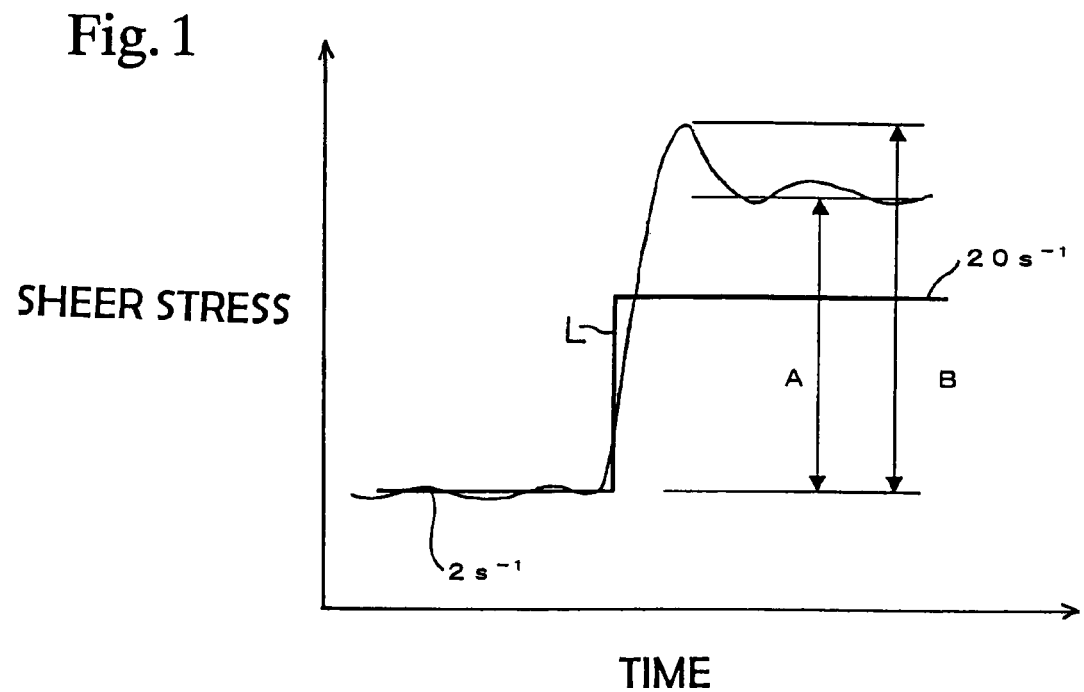
FIG. 1 is a chart showing an example of the transitional behavior of a cosmetic base subjected a steady shear deformation at a shear rate of 2 s$^{-1}$ for 100 seconds followed by a steady shear deformation at a stepwise increased shear rate of 20 s$^{-1}$.

The cosmetic base used in the present invention has such rheological characteristics that, when subjected to a steady shear deformation at a shear rate of 2 s$^{-1}$ for 100 seconds followed by a steady shear deformation at a stepwise increased shear rate of 20 s$^{-1}$, it shows no shear stress growth or shows such a shear stress growth that the difference between the peak shear stress at a shear rate of 20 s$^{-1}$ and the equilibrium shear stress at the same shear rate is 20% or smaller of the equilibrium shear stress, in the transition between the two shear deformations. This difference will be also called "stress variation". FIG. 1 presents an example of a chart showing the transitional behavior of a cosmetic base subjected to a steady shear deformation at a shear rate of 2 s$^{-1}$ for 100 seconds followed by a steady shear deformation at a stepwise increased shear rate of 20 s$^{-1}$.

The stress variation represents the rheological characteristics governing the behavior of a cosmetic base when applied and infiltrated. The characteristics of a cosmetic base having a small stress variation is governed by viscosity and can be applied and infiltrated with high accuracy. With a large stress variation, the characteristics of a cosmetic base are governed by elasticity, and release of energy stored in the elasticity term takes place after application or during infiltration, which makes it difficult to conduct the coating and impregnation step in a stable manner. The present invention is based on the finding that a cosmetic base having a stress variation of 20% or less exhibits satisfactory coating and impregnating properties when applied at a shear rate of $10^2$ to $10^6$ s$^{-1}$. The technique of the present invention is especially effective in applying and infiltrating a cosmetic base to and into a fibrous structure.

FIG. 1 represents a case in which shear stress growth occurs in a transitional stage in stepwise increasing a shear rate. The abscissa indicates time, and the ordinate shear rate and shear stress. Shear is imposed over the time period indicated by line L. As shown in FIG. 1, a steady shear deformation is applied to a cosmetic base at a shear rate of 2 s$^{-1}$ for 100 seconds. In the present embodiment, a steady shear deformation is caused by the use of concentric cylinders (cup and bob) as described infra. In this state, the shear rate is stepwise changed to 20 s$^{-1}$. In this stepwise transitional stage, the cosmetic base shows shear stress growth as depicted in FIG. 1. The shear stress growth phenomenon disappears with time, and the shear stress reaches an equilibrium A (Pa). In general, an equilibrium is reached in about 0.5 to 10 seconds. The shear stress peak of the stress growth taken as B (Pa), and the rheological characteristics of the cosmetic base used in the present invention are such that the difference between the peak B (Pa) and the equilibrium A (Pa), i.e., B−A (Pa) is 20% or smaller of the equilibrium A (Pa), i.e., (B−A)/A× 100≦20%. Where stress growth does not occur in the transitional stage in the stepwise change of shear rate, the shear rate stepwise changes with the change in shear stress.

By use of a cosmetic base having the above-described rheological characteristics, no stress remains in the applied cosmetic base after passage through a coating apparatus. As a result, the cosmetic base infiltrated into a base sheet does not undergo contraction nor suffer from thickness unevenness. The reason the shear rates before and after the stepwise change are set at 2 $s^{-1}$ and 20 $s^{-1}$, respectively, is that such conditions ensure good reproducibility and good sensitivity for detecting the shear stress growth. The same applies to the reason why the time of applying a steady shear deformation at a shear rate of 2 $s^{-1}$ is set at 100 seconds.

The rheological characteristics of a cosmetic base are measured with, for example, a rheometer Dynamic Spectrometer RDA II supplied by Rheometrics Co. In some detail, a prescribed amount of a cosmetic base is put in a sample bottle and subjected to measurement in a step rate test mode with concentric cylinders (cup diameter: 27 mm; bob diameter: 25 mm; bob length: 32 mm), etc. Specifically, shear is imposed at a shear rate of 2 $s^{-1}$ for 100 seconds. Subsequently, the shear rate is stepwise increased to 20 $s^{-1}$, and the shear stress in the transitional stage of the shear rate change is plotted. The measuring temperature is set to be the same as the coating and impregnating temperature adopted in the production of the cosmetic-impregnated sheet.

It is preferred for the cosmetic base used in the present invention to have a tanδ of 0.1 or more and less than 0.3, particularly from 0.11 to 0.28, at a shear strain of 1% and from 1 to 20, particularly 1 to 10, especially 2 to 10, at a shear strain of 500%, each measured at 0.16 Hz. This is favorable for enhancing the penetrability of the cosmetic base into the retentive sheet (described infra) when applied and also for preventing the cosmetic base from oozing out of the retentive sheet after impregnating the retentive sheet. The tanδ is measured with the rheometer described supra.

From the same standpoint described above, it is preferred for the cosmetic base used in the present invention to have a viscosity of 100 Pa·s or higher and lower than 10000 Pa·s, particularly from 200 Pa·s to 9000 Pa·s, at a shear rate of 0.03 $s^{-1}$ and from 0.1 Pa·s to 1 Pa·s, particularly 0.12 Pa·s to 0.98 Pa·s, at a shear rate of 1000 $s^{-1}$, each measured at a temperature of applying to and infiltrating into the retentive sheet. The viscosity is measured with the rheometer described supra.

From the same standpoint described above, it is also preferred for the cosmetic base used in the present invention to have a yield value of 2 to 60 Pa, particularly 5 to 50 Pa, at the temperature of applying to and infiltrating into the retentive sheet. The yield value is obtained from the flow curve plotted with a shear rate decreasing from 1000 $s^{-1}$ to 0.001 $s^{-1}$ by means of, for example, MCR300 (Paar Physica).

Components making up the cosmetic base include water; alcohols, such as ethanol and isopropyl alcohol; polyhydric alcohols as humectants, such as glycerol and sorbitol; hydrocarbons, such as solid or liquid paraffin and squalane; ester oils, such as olive oil and carnauba wax; higher fatty acids, such as stearic acid and palmitic acid; sphingosine derivatives extracted from naturally occurring substances; polysiloxanes, such as tetradecamethylpolysiloxane and methylpolysiloxane; methylpolycyclosiloxanes, such as octamethylcyclotetrasiloxane; modified silicones, such as polyether alkyl-modified silicones; anionic surface active agents, such as sulfate surface active agents; amphoteric surface active agents, such as carbobetaines; cationic surface active agents, such as mono- or dialkyl- (either straight or branched chain) added quaternary ammonium salts; and nonionic surface active agents, such as polyoxyalkylene-added polyhydric alcohols.

The cosmetic base can contain powder. Useful powders include extender pigments, such as mica and talc; inorganic pigments, such as pearlescent pigments; organic pigments, such as red #202 and red #226; and inorganic powders for UV protection, such as zinc oxide and titanium oxide. These powders may be subjected to silicone treatment, fluorine treatment, lecithin treatment, metallic soap treatment, fatty acid treatment, or alkylphosphoric ester treatment.

The cosmetic base can further contain other various ingredients that are customarily incorporated into cosmetics, quasi-drugs, drugs, and the like. Such ingredients include inorganic salts, such as magnesium sulfate; viscosity modifiers, such as polyvinyl alcohol and carboxymethyl cellulose; antiseptics, such as p-hydroxybenzoates; UV absorbers, such as p-methylbenzylidene D,L-camphor; anti-perspirants, such as allantoinchlorohydroxyaluminum; antimicrobial agents; pH adjusters; wetting agents; colorants; medicinal ingredients; perfumes; and so forth.

Figure 2:
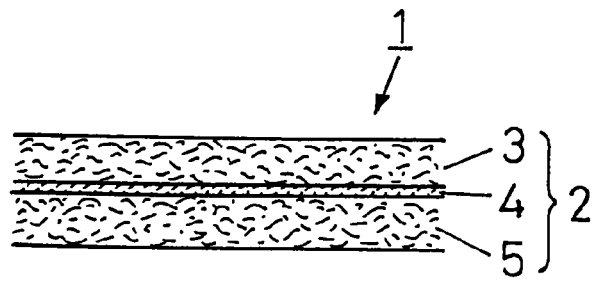
FIG. 2 is a schematic view illustrating the structure of the cosmetic-impregnated base sheet produced by a process of the present invention.

FIG. 2 shows the structure of a cosmetic-impregnated sheet 1 which is produced by the process of the present invention. The cosmetic-impregnated sheet 1 comprises a base sheet and a cosmetic base infiltrated into only one side thereof. The base sheet 2 has a three-layer laminate structure. The laminate is composed of a retentive sheet 3, a liquid impermeable sheet 4 which is superposed on one side of the retentive sheet 3, and a soft sheet 5 which is superposed on the other side of the retentive sheet 3. That is, the base sheet 2 has the liquid impermeable sheet 4 in the middle and the retentive sheet 3 and the soft sheet 5 on one side and the other side, respectively, of the liquid impermeable sheet 4. The retentive sheet 3 and the soft sheet 5 constitute the outer surfaces of the base sheet 2. The cosmetic base is infiltrated into only the retentive sheet 3.

The retentive sheet 3 which constitutes the base sheet 2 has a structure capable of absorbing a cosmetic base. The retentive sheet 3 includes porous structures and water absorbent structures. Examples of the porous or water-absorbing retentive sheet 3 include fibrous structures, such as nonwoven fabric, cloth, and knitted fabric, foamed bodies, nets, and three-dimensional molded films.

To exhibit satisfactory absorptivity for the cosmetic base, the retentive sheet 3 preferably has a density of 0.01 to 0.2 g/cm$^3$, particularly 0.06 to 0.2 g/cm$^3$. Because many cosmetic bases have a low surface energy, they are more difficult to retain in a capillary structure than aqueous bases. Therefore, it is preferred that the surface of the retentive sheet 3 be hydrophobic. More specifically, the retentive sheet 3 preferably has an ion-exchanged water contact angle of 70° or greater, particularly 85° or greater, especially 100° or greater, in view of a better balance between absorptivity and releasability for cosmetic bases.

To secure cosmetic base retentivity, the retentive sheet 3 preferably has a thickness of 0.3 to 5 mm under a load of 3.7 g/cm$^2$. From the standpoint of portability, the thickness is still preferably 0.3 to 0.8 mm.

Of the sheets recited above as a retentive sheet 3, fibrous structures are preferably used for uniform spreadability of cosmetic bases and for feel to the skin. A nonwoven fabric is still preferably used for economical considerations. Inter alia, nonwoven fabrics produced by an air-through process, a resin bond process, a spunlaced process or an airlaid process are preferred for their low density. It is particularly preferred to use a nonwoven fabric made by a spunlaced process, which has a structure allowing fibers to move, from the standpoint of uniform spreadability of cosmetic bases and for good feel to the skin.

In using a retentive sheet 3 made of a fibrous structure such as a nonwoven fabric, fibers to be used may be either hydrophilic or hydrophobic. Useful fibers include synthetic fibers, such as polyester fibers, e.g., polyethylene terephthalate (PET), acrylic fibers, e.g., polyacrylonitrile, polyamide fibers, polyolefin fibers, e.g., polypropylene (PP) and polyethylene (PE), polyurethane fiber, polyvinyl alcohol fiber, and polyfluoroethylene fiber; natural fibers, such as cotton, flax, wool, and silk; regenerated fibers, such as rayon, polynosic, and cuprammonium rayon; semisynthetic fibers, such as acetate; and fibers comprising modified products or copolymers of the above-enumerated materials. Conjugate fibers comprising two or more of these materials are also useful. The fibers may have an odd-shaped profile. A plurality of the above-described fibers may be used in combination taking into consideration the surface tension of the cosmetic base, wettability of the fiber, and the capillary diameter of the fibrous structure.

Where the retentive sheet 3 is made of the fibrous structure such as a nonwoven fabric, the constituent fibers preferably have a fineness of 0.01 to 15 denier, particularly 0.1 to 12 denier, from the viewpoint of absorptivity for cosmetic bases. While it is the most preferred for all the individual fibers making up the nonwoven fabric to have a fineness falling within the above recited range, sufficiently increased cosmetic base absorptivity is obtained only if 30% by weight or more, particularly 50% by weight or more, of the nonwoven fabric is made of fibers whose fineness falls within the range. The interfiber distance is preferably 10 to 500 μm, still preferably 20 to 300 μM, from the standpoint of absorptivity for the cosmetic base, cosmetic base releasability, and spreadability of the cosmetic base on the skin.

The interfiber distance Dp (μm) is measured as follows. Taking the thickness of a fibrous structure as y (m), the basis weight of the fibrous structure as a ($g/m^2$), the fineness of constituent fibers as F (denier), and the diameter of the constituent fibers as fd (μm), the interfiber distance Dp is represented by equation: $Dp=0.015\times\sqrt{(Fy/a)}-fd$. The thickness y of the fibrous structure is measured on a 100 mm×100 mm retentive sheet under a load of 3.7 $g/cm^2$ with Model PF-11 from Teclock. The measurement is made on five specimens for a sample to obtain an average. The constituent fiber diameter fd is measured from an enlarged photograph of fibers taken under a scanning electron microscope, and an average of five fibers is obtained. The fineness F is obtained by specifying the kind of fiber by use of a differential scanning calorimeter to find the density of the fiber ($g/m^3$) and performing calculation from equation: $F=\pi(fd/2)^2\times9000$.

Where a foamed body is used as a retentive sheet 3, the constituent materials include polyurethane resins, olefin resins such as polyethylene and polypropylene, polystyrene resins, polymethyl methacrylate, polyvinyl chloride, polyamide, unsaturated polyester, phenolic resins, rubber resins such as polybutadiene and synthetic polyisoprene, and cellulosic resins. Polyurethane resins and polyolefin resins, which are soft, low frictional, and easy to process, are preferably used. To assure an increased cosmetic base uptake, closed cell foamed bodies are preferable to open cell structures.

Where a three-dimensional molded film is used as a retentive sheet 3, a film with three-dimensional openings are preferred. It is preferred for this kind of film to have an apparent density falling within the above-recited range. Materials constituting the film include polyurethane resins, polyester resins, polyolefin resins such as polyethylene and polypropylene, polyamide resins, polyvinyl alcohol, and modified products or copolymers of these materials. It is particularly preferred to use linear low-density polyethylene or low-density polyethylene for its softness and feel to the skin.

The retentive sheet 3 preferably has a basis weight of 10 to 200 $g/m^2$, particularly 15 to 150 $g/m^2$, for securing a sufficient cosmetic base uptake and obtaining a satisfactory feel to the skin as well as from considerations for production cost.

The liquid impermeable sheet 4 is one that is capable of blocking the cosmetic base retained in the retentive sheet 3 from penetrating into the soft sheet 5 during use of the cosmetic-impregnated sheet 1. Examples of the liquid impermeable sheet 4, which is preferably oil-proof, include films of general thermoplastic resins, polyester, polyethylene, polypropylene, polyvinyl alcohol, polyvinyl chloride, polyvinylidene chloride, ethylene-vinyl acetate copolymers, polyamide, cellophane, polyetherimide, polycarbonate, polyarylate, polysultone, polyphenylene sulfide, polyether ether ketone, and like resins. For assuring heat sealability and flexibility, partially modified products or copolymers of these resins can be used. Two or more of these resins may be used as a mixture or in separate layers to make a laminate structure. In particular, stretched polypropylene films or films of high-density polyethylene or an ionomer resin are preferred for their satisfactory processability. Films of ionomer resins are especially preferred for their flexibility, sealability, pinhole resistance, and barrier properties against cosmetic bases.

The liquid impermeable sheet 4 preferably has a basis weight of 5 to 100 $g/m^2$, particularly 10 to 80 $g/m^2$, from the standpoint of sufficient barrier properties against penetration of cosmetic bases, retention of the texture of the base sheet 2, and production cost.

The soft sheet 5 is a sheet which is to come into contact with a user's hand in use of the cosmetic-impregnated sheet 1. It is not impregnated with a cosmetic base. Materials with a good texture are used as a soft sheet 5. Such a soft sheet preferably has a cloth-like texture and includes the same materials as the retentive sheet 3, such as nonwoven fabrics, woven fabrics, knitted fabrics, foamed bodies, nets, and perforated films. A nonwoven fabric is preferred for preventing a cosmetic base from going around and for assuring high porosity and a good feel to the skin.

Where nonwoven fabric is used as a soft sheet 5, the kind, basis weight, constituent fiber, fiber fineness, and other details of the nonwoven fabric used to make the retentive sheet 3 apply to the soft sheet 5. With respect to constituent fibers, polyester fibers, acrylic fibers, polyamide fibers, etc., which are hydrophobic fibers, are particularly preferred.

The base sheet 2 comprising the retentive sheet 3, the liquid impermeable sheet 4, and the soft sheet 5 preferably has a basis weight of 15 to 500 $g/m^2$, particularly 25 to 380 $g/m^2$, in view of the balance between texture and production cost.

The retentive sheet 3, the liquid impermeable sheet 4, and the soft sheet 5 are laminated together to constitute the base sheet 2. The base sheet 2 is preferably produced by extrusion lamination (sandwich lamination). This method is advantageous in that the constituent sheets hardly separate and that the liquid impermeable sheet 4 hardly contains any pinholes. Pinholes would cause the cosmetic base to penetrate into the soft sheet 5 during use of the cosmetic-impregnated sheet 1.

Figure 3:
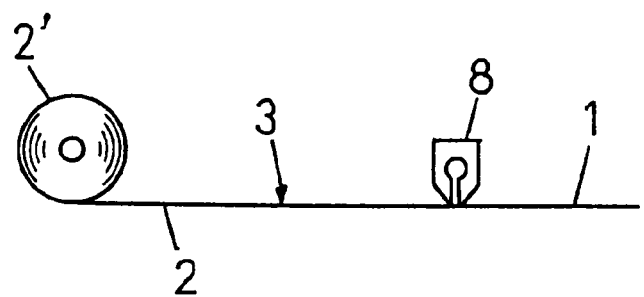
FIG. 3 shows a step involved in a process of the present invention.

A method of applying and infiltrating a cosmetic base into the retentive sheet of a base sheet will be described by referring to FIG. 3. In FIG. 3, an extrusion die coater 8 is used as a means for coating and impregnating with a cosmetic base. The base sheet 2 is unwound from a stock roll 2' of the base sheet 2 at a prescribed speed, and a cosmetic base is extruded from the slit of the die coater 8 onto the retentive sheet 3 side of the base sheet 2. Being thixotropic, the cosmetic base is controlled by a shearing force at the slit to have an appropriate viscosity and extrusion pressure and is therefore applied uniformly.

In carrying out coating and impregnation with the cosmetic base, use of the extrusion die coater is preferred for applicability to a broader range of viscosity of cosmetic bases as compared with other coating systems. The die coater is also preferred because of the closed system from cosmetic base feed up to application, which will not change the composition of the cosmetic base even if it is volatile. The die coater is also favorable because of its capability of constant rate application. The coating means to be used in the present invention is not limited to the die coater, however. For example, a reverse coater, a gravure coater, etc. are also usable.

The shear rate in extruding the cosmetic base ranges from $10^2$ to $10^6\,s^{-1}$, preferably $10^3$ to $10^5\,s^{-1}$. Shear rates lower than $10^2$ or higher than $10^6$ result in a non-uniform application, making it difficult to carry out coating and impregnation in a stable manner.

In extruding the cosmetic base, the die coater 8 may be heated to heat the cosmetic base to a prescribed temperature to thereby control the viscosity of the cosmetic base. As a matter of course, the cosmetic base may be extruded at ambient temperature with no heat applied.

The amount of the cosmetic base to be applied and infiltrated (uptake) is preferably 30 to 350 g/m$^2$, still preferably 80 to 270 g/m$^2$, for transferring the cosmetic in amounts necessary for body or facial care. For the same reason, the uptake of the cosmetic base is preferably 100 to 800% by weight, still preferably 200 to 700% by weight, based on the base sheet 2.

The cosmetic base applied to the retentive sheet 3 under the above-mentioned conditions smoothly soaks into the retentive sheet 3. According to the process of the present invention, thixotropic cosmetic bases, which are difficult to infiltrate on account of being very thixotropic, can be infiltrated with ease. Besides, the cosmetic base once infiltrated into the base sheet 2 can be applied to the skin uniformly and, even when present in small amounts, can be spread rapidly over a large area. Being thixotropic, the cosmetic base infiltrated into the base sheet 2 exists stably in the base sheet 2 with no fear of localization or seepage from the base sheet 2 in an ordinarily stored state. Accordingly, the cosmetic base is satisfactorily transferred to the skin and does not go around to the non-impregnated side, i.e., the soft sheet 5 side of the cosmetic-impregnated sheet 1 during storage. Where a plurality of cut sheets of the cosmetic-impregnated sheet 1 are packaged by, for example, pillow type packaging, the inside of the package will not be excessively wetted with the cosmetic base. Since the cosmetic base is present only in the retentive sheet 3, when the cosmetic-impregnated sheet 1 is used to apply the cosmetic base to the skin, the liquid impermeable sheet 4 prevents the cosmetic base from migrating to the soft sheet 5 and adhering to the user's hand.

The resulting cosmetic-impregnated sheet 1 is cut to size. A stack of prescribed number of the cut sheets, each folded into a prescribed shape, is packaged by, for example, pillow type packaging.

The present invention is not limited to the embodiment supra. For example, while the base sheet of the embodiment has a three-layer structure, the base sheet may have a double layer structure consisting of a retentive sheet and a liquid impermeable sheet laminated to one side of the retentive sheet and have a cosmetic base infiltrated into only the retentive sheet, or the base sheet may have a single layer structure of the retentive sheet having a cosmetic base infiltrated into only one side thereof. The details of the retentive sheet and the liquid impermeable sheet described hereinabove apply to these modifications.

In the following Examples, all the percents and parts are given by weight unless otherwise specified.

EXAMPLE 1

(1) Preparation of Cosmetic Base

An O/W cream (emulsified base) was prepared according to the formulation shown in Table 1 below. The aqueous phase except ethanol was added to the oily phase, heated to 70° C., and the mixture was cooled to room temperature over 20 minutes while stirring. Ethanol was then added, and the stirring was continued for an additional 10 minute period to obtain an O/W cream. The resulting O/W cream (cosmetic base) exhibited thixotropic properties. The other particulars were as shown in Table 2 below.

(2) Preparation of Base Sheet

Spunlaced nonwoven fabric having a basis weight of 38 g/m$^2$ was prepared from 30% PET fiber of 1.4 denier and 70% PET fiber of 0.8 denier. The resulting spunlaced nonwoven fabric had a density of 0.06 g/m$^3$, a water contact angle of 125°, and an interfiber distance of 28 μm. An ionomer resin was extruded into a film, and the spunlaced nonwoven fabric was laminated on both sides of the extruded film before the film solidified by extrusion lamination to obtain a base sheet shown in FIG. 2. The ionomer resin film had a basis weight of 33 g/m$^2$.

(3) Preparation of Cosmetic-impregnated Sheet

By use of the apparatus shown in FIG. 3, the O/W cream prepared by the method supra was extruded under the conditions shown in Table 1 and applied to and infiltrated into the retentive sheet of the base sheet prepared by the method supra to obtain a cosmetic-impregnated sheet. The coating weight was as shown in Table 1.

EXAMPLE 2

A cosmetic-impregnated sheet was obtained in the same manner as in Example 1, except that a W/O UV protection cream having the formulation shown in Table 1 was used as a cosmetic base, and the cosmetic base was extruded under the conditions shown in Table 2. The cream had thixotropic properties.

EXAMPLES 3 TO 5

Cosmetic bases having the formulations shown in Table 1 were used. These cosmetic bases exhibited thixotropic properties. Cosmetic-impregnated sheets were produced in the same manner as in Example 1, except that each of the cosmetic bases was extruded under the conditions shown in Table 2.

COMPARATIVE EXAMPLE 1

A cosmetic-impregnated sheet was obtained in the same manner as in Example 1, except for extruding the cosmetic base under the conditions shown in Table 2.

COMPARATIVE EXAMPLES 2 TO 6

Cosmetic bases having the formulations shown in Table 1 were used. Cosmetic-impregnated sheets were produced in the same manner as in Example 1, except that each of the cosmetic bases was extruded under the conditions shown in Table 2.

Evaluation of Performance:

The impregnated sheets obtained in Examples and Comparative Examples were evaluated for coating properties, penetrability and sag resistance of the cosmetic bases and appearance of the resulting impregnated sheets. The results obtained are shown in Table 2.

1) Coating Properties of Cosmetic Base

Coating properties were evaluated with respect to the running direction and the width direction of the base sheet. Cosmetic bases showing satisfactory coating properties in both the running direction and the width direction were rated A to B, those acceptable for practical use were rated C, and those unacceptable were rated D.

2) Penetrability of Cosmetic Base

Penetrability of the cosmetic base into the base sheet was evaluated apart from the evaluation on coating properties. Evaluation for penetrability differs from evaluation for coating properties because some cosmetic bases are manageably applied to a base sheet but do not sufficiently penetrate. Cosmetic bases showing sufficient penetrability were rated A to B, those acceptable for practical use were rated C, and those unacceptable were rated D.

3) Sag and Run Resistance of Cosmetic Base

About 5 ml of the cosmetic base was put on a glass plate. The glass plate was tilted at 60° from the horizontal, and sag of the cosmetic base was observed. Cosmetic bases showing little sag and run were rated A to B, those showing slight sag and run were rated C, and those showing considerable sag and run were rated D.

4) Appearance of Impregnated Sheet

The appearance of the impregnated sheet was evaluated. Apart from the coating properties and the penetrability, there are cases in which the surface of the sheet suffers from fine unevenness, skips of the cosmetic base, and the like. The impregnated sheets with a satisfactory appearance were rated A to B, those with an acceptable appearance were rated C, and those with an unacceptable appearance were rated D.

TABLE 1

(unit: part)

| | Example | | | | | Comparative Example | | | | | |
|---|---|---|---|---|---|---|---|---|---|---|---|
| | 1 | 2 | 3 | 4 | 5 | 1 | 2 | 3 | 4 | 5 | 6 |
| Liquid paraffin | 8.0 | 12.0 | 9.4 | 8.0 | 8.0 | 8.0 | 8.0 | 8.0 | 8.0 | 8.0 | 8.0 |
| Silicone oil | | 5.0 | | | | | | | | | |
| Glycerol fatty acid ester | | 1.0 | | | | | | | | | |
| Aluminum distearate | | 1.5 | | | | | | | | | |
| Polysiloxane copolymer | | 1.5 | | | | | | | | | |
| Neopentyl glycol dicaprate | 2.0 | | 2.4 | 2.0 | 2.0 | 2.0 | 2.0 | 2.0 | 2.0 | 2.0 | 2.0 |
| 1,3-Butylene glycol | 6.0 | 2.0 | 7.1 | 6.0 | 6.0 | 6.0 | 6.0 | 6.0 | 6.0 | 6.0 | 6.0 |
| Polyethylene glycol | 4.0 | 1.0 | 4.7 | 4.0 | 4.0 | 4.0 | 4.0 | 4.0 | 4.0 | 4.0 | 4.0 |
| Carboxyvinyl polymer (1) | 1.0 | | 0.5 | 1.0 | 0.5 | 1.2 | | 1.5 | 3.0 | 0.6 | 0.3 |
| Carboxyvinyl polymer (2)*[1] | | | | | | | 1.5 | | | | |
| Acrylic acid-alkyl methacrylate copolymer | 0.5 | | 0.2 | 0.5 | 0.5 | 0.5 | 0.2 | 0.2 | 0.2 | 0.2 | 0.1 |
| Sodium hydroxide aqueous solution (50%) | 0.3 | | 0.4 | 0.3 | 0.3 | 0.3 | 0.3 | 0.3 | 0.3 | 0.3 | 0.3 |
| Methyl p-hydroxybenzoate | 0.5 | 0.6 | 0.6 | 0.5 | 0.5 | 0.5 | 0.5 | 0.5 | 0.5 | 0.5 | 0.5 |
| Magnesium sulfate | | 0.8 | | | | | | | | | |
| Titanium oxide | 5.0 | 5.0 | | 5.0 | 5.0 | 5.0 | 0.3 | 5.0 | 5.0 | | |
| Ethanol | 15.0 | | | 15.0 | 15.0 | 15.0 | 15.0 | 15.0 | 15.0 | 15.0 | 15.0 |
| Purified water | 57.7 | 69.6 | 74.7 | 57.7 | 58.2 | 57.7 | 62.2 | 57.7 | 55.8 | 63.4 | 63.8 |
| Total | 100.0 | 100.0 | 100.0 | 100.0 | 100.0 | 100.0 | 100.0 | 100.0 | 100.0 | 100.0 | 100.0 |

*[1]For low viscosity

TABLE 2

| | | Example | | | | | Comparative Example | | | | | |
|---|---|---|---|---|---|---|---|---|---|---|---|---|
| | | 1 | 2 | 3 | 4 | 5 | 1 | 2 | 3 | 4 | 5 | 6 |
| | | Cosmetic Base: | | | | | | | | | | |
| Stress variation (%) at impregnation temperature | | 0*[1] | 5 | 1 | 16 | 0*[1] | 0*[1] | 1 | 23 | 50 | 0*[1] | 0*[1] |
| tanδ at 27° C. | 1% shear strain | 0.15 | 0.2 | 0.13 | 0.12 | 0.28 | 0.15 | 0.13 | 0.09 | 0.08 | 0.33 | 0.45 |
| | 500% shear strain | 5 | 12 | 8 | 3 | 9 | 5 | 8 | 1 | 0.91 | 11 | 20 |
| Viscosity at impregnation temperature (Pa·s) | 0.03 s$^{-1}$ | 800 | 5000 | 1000 | 8000 | 2000 | 800 | 1000 | 11000 | 25000 | 2000 | 1500 |
| | 1000 s$^{-1}$ | 0.2 | 0.63 | 0.12 | 0.94 | 0.15 | 0.21 | 0.17 | 1.27 | 2.5 | 0.08 | 0.05 |
| Yield value (Pa) at impregnation temp. | | 50 | 42 | 12 | 24 | 6 | 50 | 12 | 60 | 100 | 3 | 1 |

TABLE 2-continued

|  | Example | | | | | Comparative Example | | | | | |
|---|---|---|---|---|---|---|---|---|---|---|---|
|  | 1 | 2 | 3 | 4 | 5 | 1 | 2 | 3 | 4 | 5 | 6 |
| Coating and Impregnation Conditions: | | | | | | | | | | | |
| Shear rate ($s^{-1}$) | 200 | 1000 | 800000 | 1000 | 10000 | 80 | 2000000 | 1000 | 1000 | 10000 | 10000 |
| Temperature (° C.) | 20 | 20 | 20 | 20 | 20 | 20 | 20 | 20 | 20 | 20 | 20 |
| Coating weight (g/m²) | 140 | 140 | 420 | 280 | 280 | 140 | 420 | 280 | 280 | 280 | 280 |
| Coating rate (m/min) | 30 | 30 | 90 | 60 | 60 | 30 | 90 | 60 | 60 | 60 | 60 |
| Evaluation Results: | | | | | | | | | | | |
| Coating properties of cosmetic base | A | A | B | B | A | C | D | C | D | A | A |
| Penetrability of cosmetic base | A | B | A | A | A | D | B | C | D | A | A |
| Sag and run resistance of cosmetic base | A | A | A | A | B | A | A | A | A | C | D |
| Appearance of impregnated sheet | A | B | B | A | B | C–D | D | C | D | A | A |

*[1]Substantially no variation was observed.

As is apparent from the results in Tables 1 and 2, according to the process of the present invention, the cosmetics show excellent coating properties and penetrability, and the resulting impregnated sheets have a satisfactory appearance.

INDUSTRIAL APPLICABILITY

According to the process of the present invention for producing a cosmetic-impregnated sheet, a thixotropic cosmetic can easily be applied to and infiltrated into a base sheet.

The invention claimed is:

1. A process for producing a cosmetic-impregnated sheet which comprises applying and infiltrating a cosmetic base to and into a base sheet having on the surface a retentive sheet capable of absorbing and retaining the cosmetic base at a shear rate of $10^2$ to $10^6$ $s^{-1}$, wherein
   said cosmetic base is applied to and infiltrated into said retentive sheet of said base sheet, and
   said cosmetic base, when subjected to a steady shear deformation at a shear rate of 2 $s^{-1}$ for 100 seconds followed by a steady shear deformation at a stepwise increased shear rate of 20 $s^{-1}$, shows no shear stress growth or shows such a shear stress growth that a difference between the peak shear stress at a shear rate of 20 $s^{-1}$ and the equilibrium shear stress at the same shear rate is 20% or smaller of said equilibrium shear stress, in the transition between the two shear deformations,
   wherein said retentive sheet comprises a fibrous structure having a basis weight of 10 to 200 g/m² and an interfiber distance of 10 to 500 μm.

2. The process for producing a cosmetic-impregnated sheet according to claim 1, wherein said cosmetic base has a tanδ of 0.1 or more and less than 0.3 at a shear strain of 1% and from 1 to 20 at a shear strain of 500%, each measured at 0.16 Hz.

3. The process for producing a cosmetic-impregnated sheet according to claim 1, wherein said cosmetic base has a viscosity of 100 Pa·s or higher and lower than 10000 Pa·s at a shear rate of 0.03 $s^{-1}$ and from 0.1 Pa·s to 1 Pa·s at a shear rate of 1000 $s^{-1}$, each measured at a temperature of applying to and infiltrating into the retentive sheet.

4. The process for producing a cosmetic-impregnated sheet according to claim 1, wherein the retentive sheet comprises a fibrous structure.

5. The process for producing a cosmetic-impregnated sheet according to claim 1, wherein said cosmetic base has a yield value of 2 to 60 Pa.

6. A process for producing a cosmetic-impregnated sheet which comprises applying and infiltrating a cosmetic base to and into a base sheet having on the surface a retentive sheet capable of absorbing and retaining the cosmetic base at a shear rate of $10^2$ to $10^6$ $s^{-1}$, wherein
   said cosmetic base is applied to and infiltrated into said retentive sheet of said base sheet, and
   said cosmetic base, when subjected to a steady shear deformation at a shear rate of 2 $s^{-1}$ for 100 seconds followed by a steady shear deformation at a stepwise increased shear rate of 20 $s^{-1}$, shows no shear stress growth or shows such a shear stress growth that a difference between the peak shear stress at a shear rate of 20 $s^{-1}$ and the equilibrium shear stress at the same shear rate is 20% or smaller of said equilibrium shear stress, in the transition between the two shear deformations,
   wherein said base sheet comprises said retentive sheet and a liquid impermeable sheet superposed on one side of a nonwoven fabric.

7. The process for producing a cosmetic-impregnated sheet according to claim 6, wherein the liquid impermeable sheet has a basis weight of 5 to 100 g/m².

8. The process for producing a cosmetic-impregnated sheet according to claim 6, wherein said cosmetic base has a yield value of 2 to 60 Pa.

9. The process for producing a cosmetic-impregnated sheet according to claim 6, wherein the retentive sheet comprises a fibrous structure.

10. The process for producing a cosmetic-impregnated sheet according to claim 6, wherein said cosmetic base has a tanδ of 0.1 or more and less than 0.3 at a shear strain of 1% and from 1 to 20 at a shear strain of 500%, each measured at 0.16 Hz.

11. The process for producing a cosmetic-impregnated sheet according to claim 6, wherein said cosmetic base has a viscosity of 100 Pa·s or higher and lower than 10000 Pa·s at a shear rate of 0.03 $s^{-1}$ and from 0.1 Pa·s to 1 Pa·s at a shear rate of 1000 $s^{-1}$, each measured at a temperature of applying to and infiltrating into the retentive sheet.

12. A process for producing a cosmetic-impregnated sheet which comprises applying and infiltrating a cosmetic base to and into a base sheet having on the surface a retentive sheet capable of absorbing and retaining the cosmetic base at a shear rate of $10^2$ to $10^6$ s$^{-1}$, wherein said cosmetic base is applied to and infiltrated into said retentive sheet of said base sheet, and said cosmetic base, when subjected to a steady shear deformation at a shear rate of 2 s$^{-1}$ for 100 seconds followed by a steady shear deformation at a stepwise increased shear rate of 20 s$^{-1}$, shows no shear stress growth or shows such a shear stress growth that a difference between the peak shear stress at a shear rate of 20 s$^{-1}$ and the equilibrium shear stress at the same shear rate is 20% or smaller of said equilibrium shear stress, in the transition between the two shear deformations, wherein the retentive sheet comprises a fibrous structure and the fibrous structure is a nonwoven fabric having a finesse of fibers of 0.01 to 15 denier and the interfiber distance of 10 to 500 μm.

13. The process for producing a cosmetic-impregnated sheet according to claim 12, wherein said cosmetic base has a tan δ of 0.1 or more and less than 0.3 at a shear strain of 1% and from 1 to 20 at a shear strain of 500%, each measured at 0.16 Hz.

14. A process for producing a cosmetic-impregnated sheet which comprises applying and infiltrating a cosmetic base to and into a base sheet having on the surface a retentive sheet capable of absorbing and retaining the cosmetic base at a shear rate of $10^2$ to $10^6$ s$^{-1}$, wherein said cosmetic base is applied to and infiltrated into said retentive sheet of said base sheet, and said cosmetic base, when subjected to a steady shear deformation at a shear rate of 2 s$^{-1}$ for 100 seconds followed by a steady shear deformation at a stepwise increased shear rate of 20 s$^{-1}$, shows no shear stress growth or shows such a shear stress growth that a difference between the peak shear stress at a shear rate of 20 s$^{-1}$ and the equilibrium shear stress at the same shear rate is 20% or smaller of said equilibrium shear stress, in the transition between the two shear deformations, wherein the retentive sheet comprises a fibrous structure and the fibrous structure is a nonwoven fabric and at least 30 wt. % of the nonwoven fabric is made of fibers having a finesse of 0.01 to 15 denier.

15. The process for producing a cosmetic-impregnated sheet according to claim 14, wherein said cosmetic base has a tan δ of 0.1 or more and less than 0.3 at a shear strain of 1% and from 1 to 20 at a shear strain of 500%, each measured at 0.16 Hz.

16. A process for producing a cosmetic-impregnated sheet which comprises applying and infiltrating a cosmetic base to and into a base sheet having on the surface a retentive sheet capable of absorbing and retaining the cosmetic base at a shear rate of $10^2$ to $10^6$ s$^{-1}$, wherein said cosmetic base is applied to and infiltrated into said retentive sheet of said base sheet, and said cosmetic base, when subjected to a steady shear deformation at a shear rate of 2 s$^{-1}$ for 100 seconds followed by a steady shear deformation at a stepwise increased shear rate of 20 s$^{-1}$, shows no shear stress growth or shows such a shear stress growth that a difference between the peak shear stress at a shear rate of 20 s$^{-1}$ and the equilibrium shear stress at the same shear rate is 20% or smaller of said equilibrium shear stress, in the transition between the two shear deformations, wherein the retentive sheet has a density of 0.01 to 0.2 g/cm$^3$.

17. The process for producing a cosmetic-impregnated sheet according to claim 16, wherein said cosmetic base has a tan δ of 0.1 or more and less than 0.3 at a shear strain of 1% and from 1 to 20 at a shear strain of 500%, each measured at 0.16 Hz.

18. A process for producing a cosmetic-impregnated sheet which comprises applying and infiltrating a cosmetic base to and into a base sheet having on the surface a retentive sheet capable of absorbing and retaining the cosmetic base at a shear rate of $10^2$ to $10^6$ s$^{-1}$, wherein said cosmetic base is applied to and infiltrated into said retentive sheet of said base sheet, and said cosmetic base, when subjected to a steady shear deformation at a shear rate of 2 s$^{-1}$ for 100 seconds followed by a steady shear deformation at a stepwise increased shear rate of 20 s$^{-1}$, shows no shear stress growth or shows such a shear stress growth that a difference between the peak shear stress at a shear rate of 20 s$^{-1}$ and the equilibrium shear stress at the same shear rate is 20% or smaller of said equilibrium shear stress, in the transition between the two shear deformations, wherein the retentive sheet has a thickness of 0.3 to 5 mm under a load of 3.7 g/cm$^2$.

19. A process for producing a cosmetic-impregnated sheet which comprises applying and infiltrating a cosmetic base to and into a base sheet having on the surface a retentive sheet capable of absorbing and retaining the cosmetic base at a shear rate of $10^2$ to $10^6$ s$^{-1}$, wherein said cosmetic base is applied to and infiltrated into said retentive sheet of said base sheet, and said cosmetic base, when subjected to a steady shear deformation at a shear rate of 2 s$^{-1}$ for 100 seconds followed by a steady shear deformation at a stepwise increased shear rate of 20 s$^{-1}$, shows no shear stress growth or shows such a shear stress growth that a difference between the peak shear stress at a shear rate of 20 s$^{-1}$ and the equilibrium shear stress at the same shear rate is 20% or smaller of said equilibrium shear stress, in the transition between the two shear deformations, wherein the base sheet has a basis weight of 15 to 500 g/m$^2$.

\* \* \* \* \*